US012622753B2

(12) United States Patent
Messinger

(10) Patent No.: US 12,622,753 B2
(45) Date of Patent: May 12, 2026

(54) METHOD FOR TRACKING A MEDICAL TOOL DURING A MEDICAL PROCEDURE USING DEEP LEARNING

(71) Applicant: EPIDUTECH LTD., Nazareth (IL)

(72) Inventor: Daniel Messinger, Migdal HaEmek (IL)

(73) Assignee: EPIDUTECH LTD., Nazareth (IL)

( * ) Notice: Subject to any disclaimer, the term of this patent is extended or adjusted under 35 U.S.C. 154(b) by 385 days.

(21) Appl. No.: 18/273,405

(22) PCT Filed: Jan. 4, 2022

(86) PCT No.: PCT/IL2022/050011
§ 371 (c)(1),
(2) Date: Jul. 20, 2023

(87) PCT Pub. No.: WO2022/157759
PCT Pub. Date: Jul. 28, 2022

(65) Prior Publication Data
US 2024/0307125 A1 Sep. 19, 2024

Related U.S. Application Data

(60) Provisional application No. 63/139,955, filed on Jan. 21, 2021.

(51) Int. Cl.
A61B 34/20 (2016.01)
A61B 34/10 (2016.01)

(52) U.S. Cl.
CPC .............. *A61B 34/20* (2016.02); *A61B 34/10* (2016.02); *A61B 2034/102* (2016.02); *A61B 2034/2051* (2016.02)

(58) Field of Classification Search
CPC .. A61B 34/20; A61B 34/10; A61B 2034/2051
See application file for complete search history.

(56) References Cited

U.S. PATENT DOCUMENTS 5,729,129 A 3/1998 Acker
5,879,297 A 3/1999 Haynor et al.
(Continued)

FOREIGN PATENT DOCUMENTS

EP 0983018 A1 3/2000
WO 2020111936 A1 6/2020
WO 2020181006 A1 9/2020

OTHER PUBLICATIONS

PCT International Search Report for International Application No. PCT/IL2022/050011, mailed May 4, 2022, 4pp.
(Continued)

*Primary Examiner* — Rochelle D Turchen
(74) *Attorney, Agent, or Firm* — The Roy Gross Law Firm, LLC; Roy D. Gross

(57) ABSTRACT

Provided is a method for tracking a medical tool inside a subject's body during a medical procedure including receiving one or more signals from an array of magnetic sensors detecting a change in magnetic field generated by a magnetic element coupled to the medical tool, applying the received one or more signals to a deep learning algorithm, and determining, using the deep learning algorithm, the spatial location and/or orientation of the medical tool in relation to the array of sensors and/or within the body of the subject.

20 Claims, 4 Drawing Sheets

(56)     References Cited

U.S. PATENT DOCUMENTS

| | | | |
|---|---|---|---|
| 2004/0019447 A1 | 1/2004 | Shachar et al. | |
| 2008/0249395 A1* | 10/2008 | Shachar | A61B 5/062 |
| | | | 600/409 |
| 2014/0243750 A1 | 8/2014 | Larsen et al. | |
| 2014/0257080 A1 | 9/2014 | Dunbar et al. | |
| 2016/0051164 A1 | 2/2016 | Derichs et al. | |
| 2017/0319101 A1 | 11/2017 | Ruers et al. | |
| 2017/0360514 A1 | 12/2017 | Eichler et al. | |
| 2019/0104991 A1 | 4/2019 | Westerhof et al. | |
| 2019/0355149 A1 | 11/2019 | Avendi et al. | |
| 2021/0290311 A1* | 9/2021 | Fuerst | B25J 19/027 |

OTHER PUBLICATIONS

PCT Written Opinion for International Application No. PCT/IL2022/050011, mailed mailed May 4, 2022, 4pp.

PCT International Preliminary Report on Patentability for International Application No. PCT/IL2022/050011, issued Jul. 20, 2023, 5pp.

* cited by examiner

202

PROVIDING A TRACKING SYSTEM INCLUDING A MEDICAL TOOL, A MAGNETIC ELEMENT, AND AN ARRAY OF MAGNETIC SENSORS

204

RECEIVING ONE OR MORE SIGNALS FROM THE ARRAY OF MAGNETIC SENSORS

206

APPLYING THE RECEIVED ONE OR MORE SIGNALS TO ONE OR MORE DEEP LEARNING ALGORITHMS

208

DETERMINING THE SPATIAL LOCATION AND ORIENTATION OF THE MEDICAL TOOL WITHIN THE BODY

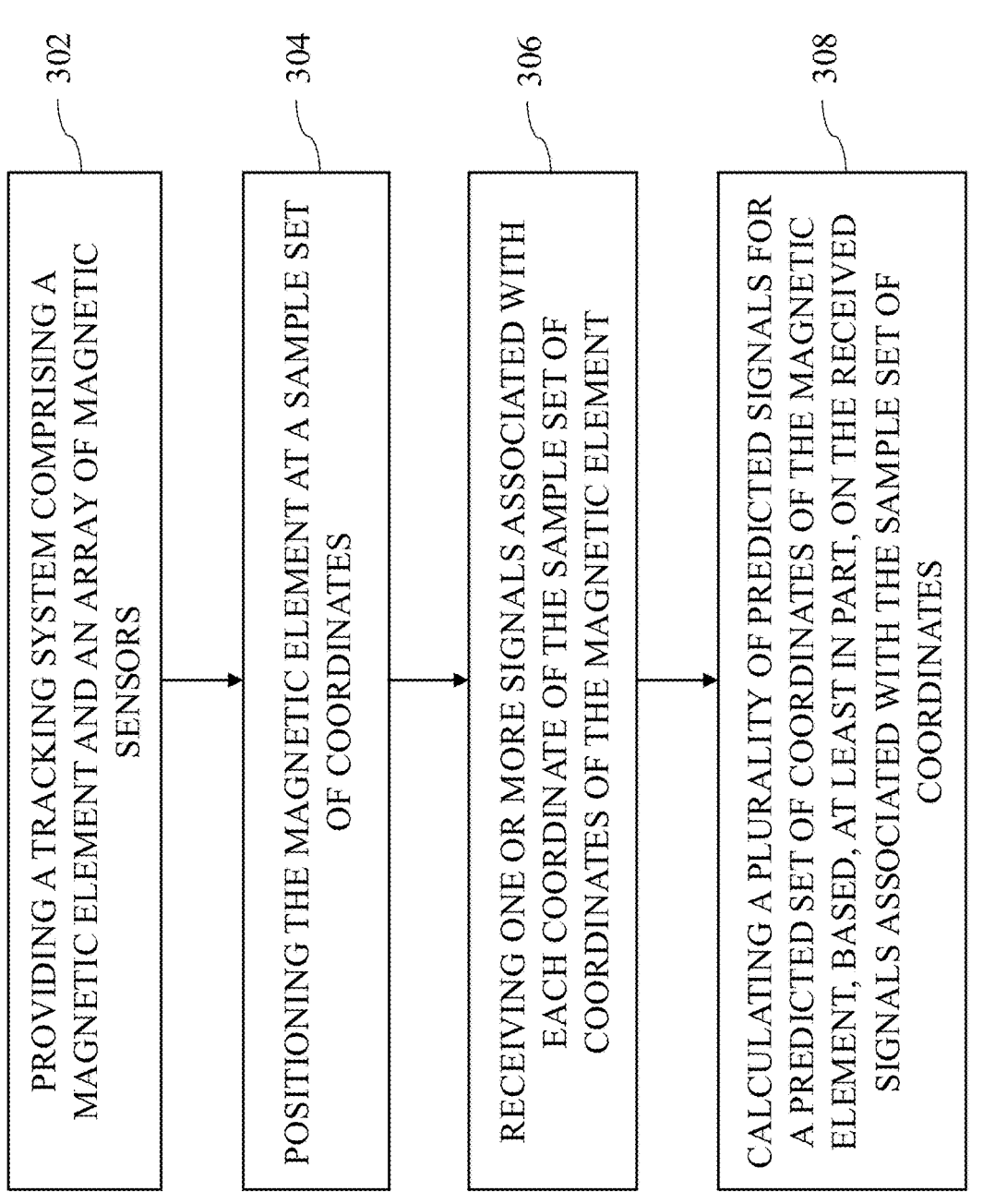

302 PROVIDING A TRACKING SYSTEM COMPRISING A MAGNETIC ELEMENT AND AN ARRAY OF MAGNETIC SENSORS

304 POSITIONING THE MAGNETIC ELEMENT AT A SAMPLE SET OF COORDINATES

306 RECEIVING ONE OR MORE SIGNALS ASSOCIATED WITH EACH COORDINATE OF THE SAMPLE SET OF COORDINATES OF THE MAGNETIC ELEMENT

308 CALCULATING A PLURALITY OF PREDICTED SIGNALS FOR A PREDICTED SET OF COORDINATES OF THE MAGNETIC ELEMENT, BASED, AT LEAST IN PART, ON THE RECEIVED SIGNALS ASSOCIATED WITH THE SAMPLE SET OF COORDINATES

FIG. 3

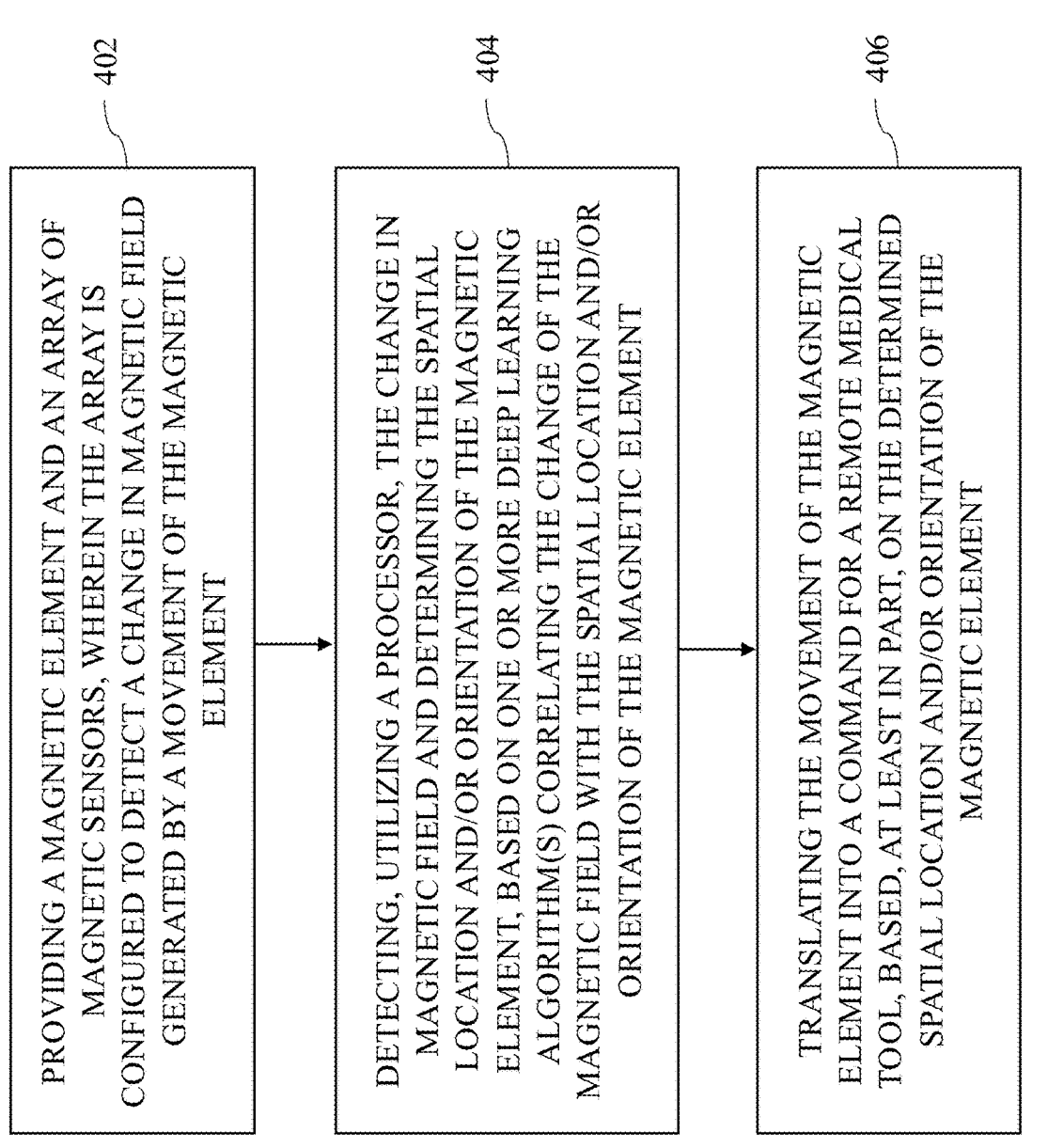

402

PROVIDING A MAGNETIC ELEMENT AND AN ARRAY OF MAGNETIC SENSORS, WHEREIN THE ARRAY IS CONFIGURED TO DETECT A CHANGE IN MAGNETIC FIELD GENERATED BY A MOVEMENT OF THE MAGNETIC ELEMENT

404

DETECTING, UTILIZING A PROCESSOR, THE CHANGE IN MAGNETIC FIELD AND DETERMINING THE SPATIAL LOCATION AND/OR ORIENTATION OF THE MAGNETIC ELEMENT, BASED ON ONE OR MORE DEEP LEARNING ALGORITHM(S) CORRELATING THE CHANGE OF THE MAGNETIC FIELD WITH THE SPATIAL LOCATION AND/OR ORIENTATION OF THE MAGNETIC ELEMENT

406

TRANSLATING THE MOVEMENT OF THE MAGNETIC ELEMENT INTO A COMMAND FOR A REMOTE MEDICAL TOOL, BASED, AT LEAST IN PART, ON THE DETERMINED SPATIAL LOCATION AND/OR ORIENTATION OF THE MAGNETIC ELEMENT

FIG. 4

METHOD FOR TRACKING A MEDICAL TOOL DURING A MEDICAL PROCEDURE USING DEEP LEARNING

CROSS REFERENCE TO RELATED APPLICATIONS

This application is a National Phase of PCT Patent Application No. PCT/IL2022/050011 having International filing date of Jan. 4, 2022, which claims the benefit of priority of U.S. Provisional Patent Application No. 63/139,955, filed Jan. 21, 2021, the contents of which are all incorporated herein by reference in their entirety.

FIELD OF THE INVENTION

The present invention, in some embodiments thereof, relates to tracking methods for tracking of medical tools during a surgical procedure using deep learning, and, more particularly, but not exclusively, to magnetic tracking methods including a magnetic element and an array of magnetic sensors.

BACKGROUND

In certain cases of minimal invasive surgery, the surgical procedure is performed by inserting a medical device into the body through a small cut in the skin of the subject. The target region of the surgery can therefore be difficult to access and may be blocked from the visual field of the physician performing the surgery. Systems for tracking of medical tools within the body during operation usually include one or more sensors configured to measure a distance from the medical tool. Thus, techniques for determining the position of the medical tool during operations have a limited accuracy due to the limitations of the resolution of signals received from the sensors as well as the accuracy of the mathematical formulas used in the calculation.

Thus, there is a need in the art for improved tracking systems and methods that can allow an accurate, reliable detection and tracking of medical tools during a surgical procedure.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with some embodiments, a method for tracking a medical tool during a medical procedure, the method includes providing a tracking system which includes a medical tool having a magnetic element, and an array of magnetic sensors, wherein the array is configured to detect a change in magnetic field generated by the movement of the magnetic element within the body, and determining, utilizing a processor, the spatial location and/or orientation of the medical tool within the body, based on one or more deep learning algorithms correlating the change of the magnetic field with the spatial location and/or orientation of the magnetic element.

There is provided, in accordance with some embodiments, a system for tracking a medical tool during a medical procedure, the system including: a medical tool including a magnetic element, an array of magnetic sensors, the array is configured to detect a change in magnetic field generated by the movement of the magnetic element within the body, and a processor configured to receive the detected change in magnetic field and determine the spatial location and/or orientation of the medical tool, based on one or more deep learning algorithm(s) correlating the change of the magnetic field with the spatial location and/or orientation of the magnetic element.

Advantageously, the array of magnetic sensors may be wirelessly associated with the magnetic element and/or the medical tool, thereby enabling the user (for example, a physician/operator of the medical tool to freely operate without physical limitations that would have been present if the array of magnetic sensors would have been mechanically coupled to the medical tool.

Advantageously, the array of magnetic sensors may be configured to detect a change in magnetic field generated by the movement of the magnetic element, thereby enabling the detection of the position of the medical tool without a need to apply a magnetic field in the operation room, and thereby allowing the user to detect the position of the medical tool without causing interference to other devices in the operation room during a medical procedure.

Advantageously, the method may include detecting the spatial location and/or orientation of the medical tool inside a subject's body during a medical procedure using one or more deep learning algorithms and therefore does not require applying the one or more signals received from the sensor array to a mathematical formula, thus increasing the resolution of the determined spatial location and/or orientation in relation to tracking methods which use mathematical formulas.

According to some embodiments there is provided a system for tracking a medical tool during a medical procedure, the system including: a tracking system including: a magnetic element configured to be placed onto a remote control, and an array of magnetic sensors, wherein the array is configured to detect a change in magnetic field generated by the movement of the magnetic element, and a processor configured to receive the detected change in magnetic field and determine the spatial location and/or orientation of the medical tool, based on one or more deep learning algorithm (s) correlating the change of the magnetic field with the spatial location and/or orientation of the magnetic element.

According to some embodiments there is provided a system for operating a remote medical tool, the system including: a magnetic element, an array of magnetic sensors, wherein the array is configured to detect a change in magnetic field generated by a movement of the magnetic element, and a processor configured to: detect the change in magnetic field and determining the spatial location and/or orientation of the magnetic element, based on one or more deep learning algorithm(s) correlating the change of the magnetic field with the spatial location and/or orientation of the magnetic element, and translate the movement of the magnetic element into a command for a remote medical tool, based, at least in part, on the determined spatial location and/or orientation of the magnetic element.

According to some embodiments there is provided a system for tracking a medical tool during a medical procedure, the system including: a medical tool including a magnetic element, an array of magnetic sensors, the array is configured to detect a change in magnetic field generated by the movement of the magnetic element within the body, and a processor configured to receive the detected change in magnetic field and determine the spatial location and/or orientation of the medical tool, based on one or more deep learning algorithm(s) correlating the change of the magnetic field with the spatial location and/or orientation of the magnetic element. According to some embodiments there is provided a method for tracking a medical tool during a medical procedure, the method including: providing a tracking system including a medical tool including a magnetic element, and an array of magnetic sensors, wherein the array is configured to detect a change in magnetic field generated by the movement of the magnetic element within the body, and determining, utilizing a processor, the spatial location and/or orientation of the medical tool within the body, based on deep learning algorithm(s) correlating the change of the magnetic field with the spatial location and/or orientation of the magnetic element.

According to some embodiments there is provided a method for operating a remote medical tool, the method including: providing a magnetic element and an array of magnetic sensors, wherein the array is configured to detect a change in magnetic field generated by a movement of the magnetic element, detecting, utilizing a processor, the change in magnetic field and determine the spatial location and/or orientation of the magnetic element, based on one or more deep learning algorithm(s) correlating the change of the magnetic field with the spatial location and/or orientation of the magnetic element, and translating the movement of the magnetic element into a command for a remote medical tool, based, at least in part, on the determined spatial location and/or orientation of the magnetic element.

According to some embodiments, the magnetic element is asymmetric.

According to some embodiments, the medical tool is manipulatable in 3 to 6 degrees of freedom.

According to some embodiments, the magnetic element is positioned along a middle portion of the medical tool.

According to some embodiments, the magnetic element is positioned in a distal portion of the medical tool.

According to some embodiments, the magnetic element is positioned in a proximal portion of the medical tool.

According to some embodiments, the method includes a plurality of magnetic elements each independently positioned in a distal portion, proximal portion, or a middle portion of the medical tool.

According to some embodiments, determining the spatial location and/or orientation of the medical tool includes compensating for a dimension of the medical tool in relation to the location of the magnetic element in relation to the medical tool.

According to some embodiments, the sensor array is configured in cartesian, radial, or cylindrical coordinate system.

According to some embodiments, the sensor array is configured to wirelessly associate with the magnetic element and/or the medical tool.

According to some embodiments, determining the spatial location and/or orientation of the medical tool includes compensating for variations in the magnetic field associated with one or more of a type of tissue, a type of procedure, a type of medical tool, and characteristics of the subject.

According to some embodiments, the characteristics of the subject include one or more of the age, gender, weight and medical history of the subject.

According to some embodiments, the method includes registering the determined spatial location and/or orientation of the medical tool within the body to a scan of the subject.

According to some embodiments, the precision between the determined spatial location and/or orientation and the actual location and/or orientation is smaller than 1.0 mm.

According to some embodiments, the processor is configured to train the deep learning algorithm on a training set including a database associated with the changes of the magnetic field due to a change of one or more coordinates of the magnetic element.

According to some embodiments, the database includes data obtained by receiving one or more signals associated with a change of the magnetic field generated by a change in the spatial location and/or orientation of the magnetic element between a plurality of pairs of coordinates.

According to some embodiments, the database includes data sets obtained using the array of magnetic sensors, and wherein each of the data sets includes three signals from each individual sensor of the array of magnetic sensors for each change in spatial location or orientation of the magnetic element.

According to some embodiments, the three signals include changes in the magnetic field generated in an x-axis, y-axis, and z-axis generated by the magnetic element.

According to some embodiments, the change in the spatial location and/or orientation of the magnetic element includes a translation of the magnetic element in one or more axes at a specified distance.

According to some embodiments, the specified distance includes between 1 to 10 millimeters.

According to some embodiments, the change in the spatial location and/or orientation of the magnetic element includes a rotation of the magnetic element at a specified degree of rotation.

According to some embodiments, the specified degree of rotation includes between 1 to 5 degrees.

According to some embodiments, the rotation of the magnetic element includes rotation about at least one of a longitudinal axis of the magnetic element, a lateral axis of the magnetic element, and a vertical axis of the magnetic element.

According to some embodiments, the database includes between 100 to 800,000,000 data sets.

According to some embodiments, each data set is obtained within 0.25 to 2 seconds.

According to some embodiments, the magnetic element is positioned on the medical tool such that it is configured to be inserted into the subject's body.

According to some embodiments, the magnetic element is positioned on the medical tool such that it is configured to remain outside the subject's during the medical procedure.

According to some embodiments, the database is generated by: providing the tracking system including the magnetic element and the array of magnetic sensors, positioning the magnetic element at a sample set of coordinates, receiving one or more signals associated with each coordinate of the sample set of coordinates of the magnetic element, and calculating a plurality of predicted signals for a predicted set of coordinates of the magnetic element, based, at least in part, on the received signals associated with the sample set of coordinates, wherein the coordinates of the predicted set of coordinates are different from coordinates of the sample set of coordinates.

According to some embodiments, the sample set of coordinates includes a plurality of different spatial locations and/or plurality of orientations of the magnetic element in relation to the array.

According to some embodiments, the predicted set of coordinates includes a plurality of spatial locations and/or plurality of orientations of the magnetic element in relation to the array.

According to some embodiments, the sample set of coordinates includes a plurality of coordinates with a same x-axis value and a same y-axis value, wherein the z-axis value of two or more different coordinates in the sample set of coordinates is different.

According to some embodiments, the sample set of coordinates includes a plurality of coordinates having a same x-axis value, a same y-axis value, a same z-axis value, and a different orientation (or different degree of rotation) in relation to the array.

According to some embodiments, the sample set of coordinates includes about 1 to 6 coordinates.

According to some embodiments, the deep learning algorithm is further configured to determine the spatial location and/or orientation of a plurality of medical tools within the body.

According to some embodiments, the algorithm is further configured to determine the spatial location and/or orientation of a plurality of medical tools within the body using superposition of the signals saved within the database.

According to some embodiments, the remote medical tool includes a motor configured to receive the command from the processor and operate the remote medical tool.

According to some embodiments, the method further includes generating a simulation of a medical operation, wherein the remote medical tool is a simulated medical tool in the simulation of a medical operation, and wherein translating the movement of the magnetic element into a command includes displaying the movement of the simulated medical tool in the simulated medical operation.

According to some embodiments, translating the movement of the magnetic element into a command further includes adjusting the proportion between the movement of the magnetic element and the command such that movement of the remote medical tool may be proportionately smaller or larger than the movement of the magnetic element.

In addition to the exemplary aspects and embodiments described above, further aspects and embodiments will become apparent by reference to the figures and by study of the following detailed description.

BRIEF DESCRIPTION OF THE FIGURES

Some exemplary implementations of the methods and systems of the present disclosure are described with reference to the accompanying drawings. In the drawings, like reference numbers indicate identical or substantially similar elements.

FIG. 3 shows a flowchart of functional steps in a method for generating a database, in accordance with some embodiments of the present invention; and FIG. 4 shows a flowchart of functional steps in a method for operating a remote medical tool, in accordance with some embodiments of the present invention.

DETAILED DESCRIPTION

Figure 1:
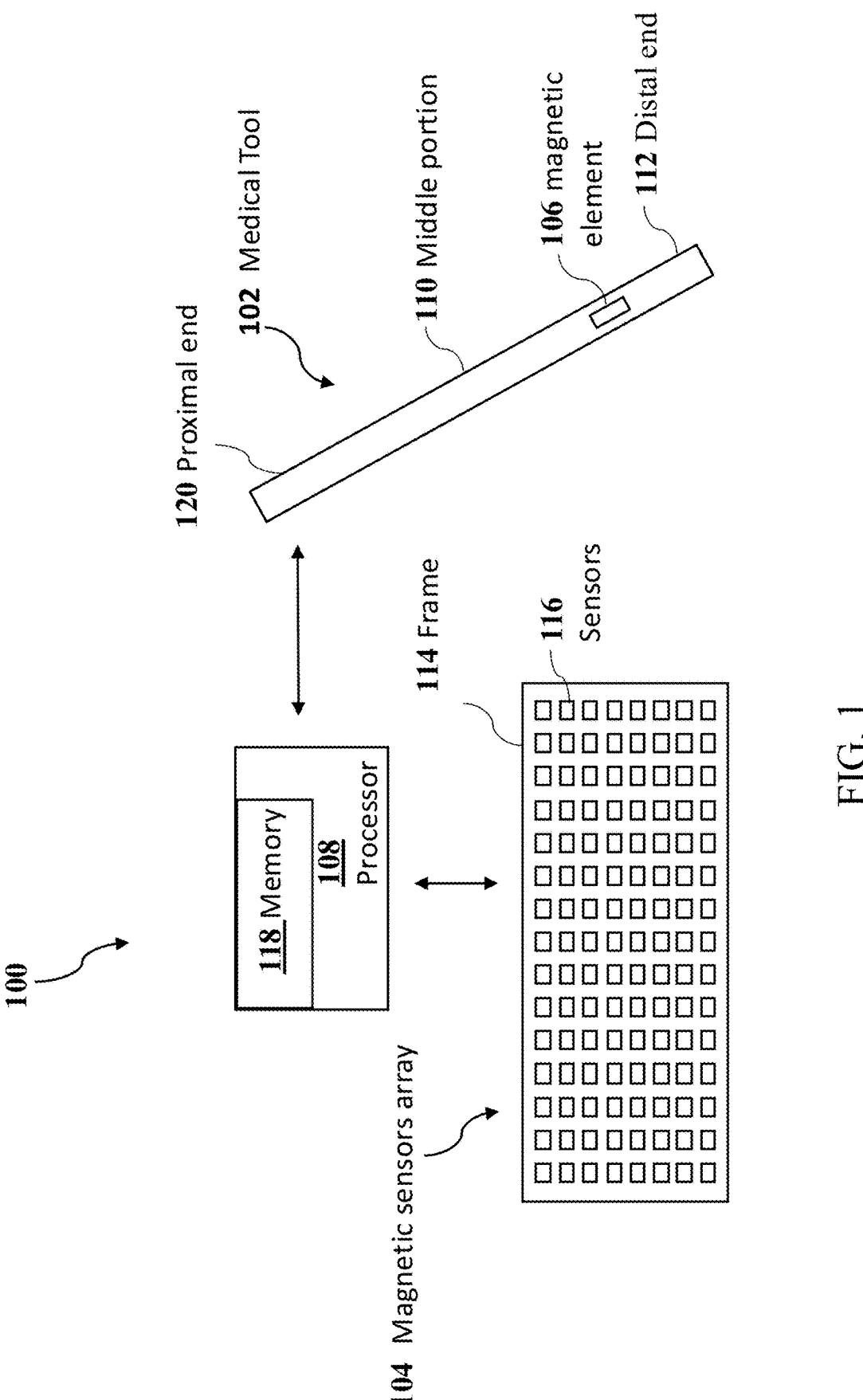
FIG. 1 shows a schematic illustration of an exemplary tracking system, in accordance with some embodiments of the present invention.

According to an aspect of some embodiments of the present invention there is provided a system and method for tracking a medical tool inside a subject's body during a medical procedure.

According to some embodiments of the present invention there is provided a tracking system configured to identify a spatial location and/or orientation of a medical tool within the body of a subject, based on deep learning algorithms correlating the change of the magnetic field with the spatial location and/or orientation of a magnetic element coupled to the medical tool. According to some embodiments, the tracking system may include an array of magnetic sensors configured to be positioned near the subject during operation and to detect a change of the magnetic field of the magnetic element. According to some embodiments, the tracking system may include a processor in communication with the array of magnetic sensors and configured to apply one or more signals received from the array of magnetic sensors to one or more deep learning algorithms. According to some embodiments, the deep learning algorithms may be configured to identify the spatial location and/or orientation of a medical tool based, at least in part, on the received one or more signals.

According to some embodiments of the present invention there is provided a method for tracking a medical tool inside a subject's body during a medical procedure. According to some embodiments, the method may include receiving one or more signals from the array of magnetic sensors. According to some embodiments, the method may include applying the received one or more signals to one or more deep learning algorithms configured to determine the spatial location and/or orientation of the medical tool in relation to the array of sensors and/or within the body of the subject. According to some embodiments, the method may include registering the determined spatial location and/or orientation of the medical tool within the body to a scan of the subject in real time.

According to some embodiments of the present invention there is provided a method for tracking a medical tool inside a subject's body during a medical procedure using one or more deep learning algorithms. According to some embodiments, the one or more deep learning algorithms may be configured to receive three signals from one or more individual sensors of the array of magnetic sensors, wherein each of the three signals may be associated with one or more of the x-axis, y-axis, and z-axis of the change of the magnetic field generated by the magnetic element in relation to the array of magnetic sensors. According to some embodiments, the one or more deep learning algorithms may be configured to determine spatial location and/or orientation of the medical tool based, at least in part, on the received signals. According to some embodiments, the method may include determining the spatial location and/or orientation of the medical tool based without applying the one or more signals received from the sensor array to a mathematical formula.

According to some embodiments of the present invention there is provided a deep learning algorithm configured to determine spatial location and/or orientation of the medical tool, wherein the deep learning algorithm may be trained on a training set including a database having a plurality of data sets associated with changes in the magnetic field caused by a change in the spatial location and/or orientation of the magnetic element in relation to the array of magnetic sensors. According to some embodiments, the each of the data sets may include a change in the coordinates of the magnetic element, such as, translation of the magnetic element along the x-axis, the y-axis, and/or the z-axis, and/or rotation of the magnetic element about a longitudinal axis, a lateral axis, and/or a vertical axis thereof. According to some embodiments, the each of the data sets may include data associated with a change in the magnetic field generated by the change in the coordinates of the magnetic element.

Reference is made to FIG. 1, which shows a schematic illustration of an exemplary tracking system, in accordance with some embodiments of the present invention. According to some embodiments, the tracking system 100 may include a medical tool 102 and an array of magnetic sensors 104. According to some embodiments, the tracking system 100 and/or the medical tool 102 may include one or more magnetic elements 106. According to some embodiments, the array of magnetic sensors 104 may be configured to detect a change in magnetic field generated by a movement of the magnetic element 106. According to some embodiments, the tracking system 100 may include a processor 108 in communication with the array of magnetic sensors 104. According to some embodiments, the processor 108 may be configured to output data associated with a location and/or orientation of the medical tool 102. According to some embodiments, the array of magnetic sensors 104 may be wirelessly coupled to the processor 108. According to some embodiments, the medical tool 102 may be manipulatable in at least 6 degrees of freedom. According to some embodiments, the medical tool 102 may be manipulated by automatically via a processor, such as processor 108, or may be manipulated by a user. According to some embodiments, the processor 108 may be in communication with a memory module 118. According to some embodiments, the memory module 118 may include instructions for executing a method for tracking the medical tool 102 inside a subject's body during a medical procedure.

According to some embodiments, the array of magnetic sensors 104 may be configured to wirelessly associate with the magnetic element 106 and/or the medical tool 102, such that the detection of the magnetic element 106 via the array of magnetic sensors 104 does not require a mechanical coupling therebetween. Advantageously, having an array of magnetic sensors 104 that is wirelessly associated with the magnetic element 106 and/or the medical tool 102 enables the physician/operator of the medical tool to freely operate without physical limitations that would have been present if the array of magnetic sensors 104 would have been coupled to the medical tool 102 via a cable, for example.

According to some embodiments, the medical tool 102 may be configured to support the magnetic element 106. According to some embodiments, the medical tool 102 may be coupled to the magnetic element 106 such that the position of the magnetic element 106 may be fixed in relation to the medical tool 102. According to some embodiments, the medical tool 102 may be coupled to the magnetic element 106 such that the orientation of the magnetic element 106 may be fixed in relation to the orientation of the medical tool 102. According to some embodiments, the magnetic element 106 may be positioned along a middle portion 110 of the medical tool 102. According to some embodiments, the magnetic element 106 may be positioned between a distal end 112 of the medical tool 102 and a proximal end 120 of the medical tool 102. According to some embodiments, the magnetic element 106 may include an asymmetric shape. According to some embodiments, the magnetic element 106 may be asymmetric along at least one or more planes of symmetry. According to some embodiments, the magnetic element 106 may include a plurality of separated magnetic elements.

According to some embodiments, the medical tool 102 may include one or more tools configured to insert into the body of the subject. According to some embodiments, the medical tool 102 may include a tool configured for electrocautery configured to coagulate blood vessels and vaporize soft tissues. According to some embodiments, the medical tool 102 may include a drill, such as a mechanical or electrical drill, for example, a drill configured to drill through bone tissue. According to some embodiments, the medical tool 102 may include a shaver, such as, a mechanical or electrical shaver. According to some embodiments, the shaver may be configured to remove soft tissues such as intervertebral disc material and ligaments. According to some embodiments, the medical tool 102 may include one or more periosteal stripper, for example, configured for blunt dissection of soft tissues, and helpful in separating adhesions and scars. According to some embodiments, the medical tool 102 may include one or more optic fibers configured to allow direct visualization of the epidural content, including scars, nerves and the degree of decompression. According to some embodiments, the medical tool 102 may be interchangeable. According to some embodiments, the medical tool 102 may include a controllable robot. According to some embodiments, the medical tool 102 may be manipulatable using a robot and/or robotic arm. According to some embodiments, the medical tool 102 may include an accelerometer. According to some embodiments, the accelerometer may be in communication with the processor 108, and may be configured to identify the spatial location and/or orientation of the medical tool 102.

According to some embodiments, the array of magnetic sensors 104 may include a frame 114 configured to be positioned near or abutting to a subject during a medical procedure. According to some embodiments, the array of magnetic sensors 104 may include a plurality of sensors 116 configured to detect a magnetic field and positioned on the frame 114. According to some embodiments, the positions of the plurality of sensors 116 are fixed in relation to the frame 114.

According to some embodiments, during a procedure, the medical tool 102 may be inserted into the body of the subject such that the magnetic element 106 is not visible to the physician/operator. According to some embodiments, the array of magnetic sensors 104 may include a plurality of sensors 116 configured to detect a change in magnetic field generated by the movement of the magnetic element 106 within the body of the subject, such as during a medical operation in which the medical tool 102, the distal end of the medical tool 102, and/or the magnetic element 106 cannot be visually tracked by the physician/operator.

Advantageously, an array of magnetic sensors configured to detect a change in magnetic field generated by the movement of the magnetic element enables detection of the position of the medical tool without needing to apply a magnetic field in the operation room, thereby allowing a physician/operator to detect the position of the medical tool without causing interference to other devices in the operation room during a procedure.

According to some embodiments, the array of magnetic sensors 104 and/or the plurality of sensors 116 may include 256 sensors. According to some embodiments, the array of magnetic sensors 104 may be positioned in a matrix along the frame 114. For example, in some embodiments, the matrix may include 8 rows. For example, in some embodiments, the row may include 32 magnetic sensors.

According to some embodiments, the plurality of sensors 116 may include magnetic sensors configured to detect changes and/or disturbances in the strength, direction, and/or flux of the magnetic element 106. According to some embodiments, the plurality of sensors 116 may include magnetic sensors configured to detect a magnitude of the magnetic vector produced by the magnetic element 106. According to some embodiments, the plurality of sensors 116 may include magnetic sensors configured to detect a change in the magnitude of the magnetic vector produced by the magnetic element 106. According to some embodiments, the plurality of sensors 116 may include low-field magnetic sensors. According to some embodiments, one or more of the plurality of sensors 116 may be configured to detect a magnetic field having the strength of −1200 μT(Typ) to 1200 μT(Typ). According to some embodiments, one or more of the plurality of sensors 116 may a magnetic sensitivity of at least 0.042 μT/LSB(Typ). According to some embodiments, the magnetic sensitivity of one or more of the plurality of sensors 116 may range between 0.05 μT/LSB(Typ) and 0.03 μT/LSB(Typ) According to some embodiments, the array of magnetic sensors 104 may be configured in one of a cartesian and cylindrical coordinate system. According to some embodiments, the frame 114 may include a flat plate, a curved plate, a cylindrical or tubular shape, and the like. According to some embodiments, the plurality of sensors 116 may be positioned along the frame 114 as to form one of a cartesian and cylindrical coordinate system.

According to some embodiments, the processor 108 may be in communication with the plurality of sensors 116. According to some embodiment, the processor 108 may be configured to receive one or more signals from the plurality of sensors 116. According to some embodiments, the one or more signals may be associated with a change in the magnetic field due to movements of the magnetic element 106. According to some embodiments, the one or more signals may include a change in strength, direction, and/or flux of the magnetic field. According to some embodiments, the one or more signals may include a magnitude of the magnetic vector detected by one or more of the plurality of sensors 116.

According to some embodiments, the processor 108 may be configured to receive individual signals from individual sensors of the plurality of sensors 116. According to some embodiments, the processor 108 may be configured to apply the received one or more signals to a deep learning algorithm stored in the memory module 118 which then outputs the position of the medical tool 102 and/or the magnetic element 106 based, at least in part, on the received one or more signals.

According to some embodiments, the memory module 118 may be coupled to the processor 108 via a cable or wirelessly. According to some embodiments, the memory module 118 may include a database including data associated with the changes magnetic field due to movements of the magnetic element 106. According to some embodiments, and as described in greater detail elsewhere herein, the database may include data associated with any one or more of a change in strength, direction, and/or flux of the magnetic element 106 for a movement from a first position to a second position in relation to the array of magnetic sensors 104. According to some embodiments, and as described in greater detail elsewhere herein, the database may include data associated with the change of the magnitude of the magnetic vector produced by the magnetic element 106 for a movement from a first position to a second position in relation to the array of magnetic sensors 104. According to some embodiments, the memory module 118 may include instructions for receiving one or more signals from the plurality of sensors 116 and/or the array of magnetic sensors 104. According to some embodiments, the memory module 118 may include instructions for applying the received signals to the deep learning algorithm stored thereon.

According to some embodiments, the processor 108 may be configured to train the deep learning algorithm on a training set. According to some embodiments, the training set may include the database. According to some embodiments, the database may include data associated with changes of the magnetic field due to movements of the magnetic element. According to some embodiments, the database may include data obtained by receiving one or more signals associated with a change of the magnetic field due to a change in the spatial location and/or orientation of the magnetic element between a plurality of positions of the magnetic element. According to some embodiments, the database may include data sets obtained using the array of magnetic sensors. According to some embodiments, each data set may include coordinates associated with a change in the translation along the x-axis, the y-axis, and the z-axis.

According to some embodiments, each of the data sets comprises three signals for each individual sensor of the array of magnetic sensors for each change in spatial location or orientation of the magnetic element between a plurality of positions of the magnetic element. According to some embodiments, the three signals include changes in the magnetic field generated in an x-axis, y-axis, and z-axis of the change of the magnetic field generated by the magnetic element in relation to the array of magnetic sensors, respectively. According to some embodiments, at least two of the x-axis, y-axis, and z-axis may be defined as the normals of perpendicular planes or non-perpendicular planes. According to some embodiments, the x-axis, y-axis, and/or z-axis may be defined in relation to any one or more of the frame 114 and at least one sensor of the plurality of sensors 116.

According to some embodiments, the change in spatial location or orientation of the magnetic element between a plurality of positions of the magnetic element may include a change in the spatial location or orientation of the magnetic element when the magnetic element is moved from a first position to a second position. For example, the database may include data associated with a change in magnetic field generated when the magnetic element is moved from a first position to a second position and/or from a second position to a third position, etc. According to some embodiments, the change in the spatial location and/or orientation of the magnetic element between two positions of the magnetic element includes a translation of the magnetic element in one or more axes at a specified distance, for example, one or more of the x-axis, the y-axis, and the z-axis. According to some embodiments, the specified distance includes between 1 to 10 millimeters. According to some embodiments, the specified distance may be constant for different data sets associated with translations of the magnetic element. According to some embodiments, the specified distance may vary between different data sets associated with translations of the magnetic element. According to some embodiments, each data set may include coordinates associated with a change in the translation along the x-axis, the y-axis, and the z-axis and/or a change in the degree of rotation about the longitudinal axis of the magnetic element the lateral axis of the magnetic element and the vertical axis of the magnetic element.

According to some embodiments, the ratio between the accuracy of the determined spatial location and/or orientation and the specified distance is between 1:5 to 1:15. According to some embodiments, the ratio between the accuracy of the determined spatial location and/or orientation and the specified distance is 1:10. For example, for a database having data sets with a translation of a specified distance of 10 mm, the accuracy of the determined spatial location and/or orientation is 1 mm. For example, for a database having data sets with a translation of a specified distance of 6 mm, the accuracy of the determined spatial location and/or orientation is 0.6 mm.

According to some embodiments, the change in the spatial location and/or orientation of the magnetic element between two positions of the magnetic element includes a rotation of the magnetic element at a specified degree of rotation. According to some embodiments, the specified degree of rotation may include between 1 to 5 degrees. According to some embodiments, the rotation of the magnetic element may include a rotation about at least one of a longitudinal axis of the magnetic element, a lateral axis of the magnetic element, and a vertical axis of the magnetic element. According to some embodiments, each data set may include coordinates associated with a change in the degree of rotation about the longitudinal axis of the magnetic element the lateral axis of the magnetic element and the vertical axis of the magnetic element.

According to some embodiments, the specified degree of rotation may be constant for different data sets associated with rotations of the magnetic element. According to some embodiments, the specified degree of rotation may be constant for different data sets associated with rotations of the magnetic element in a same axis.

For example, in some embodiments, the specified degree of rotation about the x-axis may be the same for each change in positions associated with rotations of the magnetic element. According to some embodiments, the specified degree of rotation may vary between different data sets associated with rotations of the magnetic element. According to some embodiments, the specified degree of rotation may vary between different data sets associated with rotations of the magnetic element about different axes. For example, in some embodiments, the specified degree of rotation may be constant for rotations about the x-axis and different than the specified degree of rotation about the z-axis.

According to some embodiments, one or more data set of the database may be obtained within 0.25 to 2 seconds. According to some embodiments, the velocity of movement between two positions of the magnetic element of one or more of data set may be 10-100 mm per second. According to some embodiments, the database may include between 100 to 800,000,000 data sets. Advantageously, the database may include a sufficient amount of data sets such that the deep learning algorithm may be trained to identify the spatial location and/or orientation of the magnetic element by identifying the change in the magnetic field generated by the magnetic element. Advantageously, the database may include a sufficient amount of data sets such that the deep learning algorithm may be trained to identify a spatial location and/or orientation that is not represented by the data within the database. For example, the deep learning algorithm may be configured to identify a spatial location and/or orientation of the magnetic element that is associated with a midpoint between a spatial location and/or orientation of two data sets of the database.

According to some embodiments, the database may be generated automatically by extrapolating one or more data sets based, at least in part, on one or more obtained data sets. According to some embodiments, the database may be generated by providing the tracking system including the magnetic element and the array of magnetic sensors and positioning the magnetic element at a sample set, or in other words, sample set of coordinates. According to some embodiments, the sample set (of coordinates) may include one or more of the obtained data sets. According to some embodiments, the database may be generated by receiving one or more signals associated with each coordinate of the sample set of the magnetic element, or in other words, receiving signals associated with one or more of data set (which may be obtained as described in greater detail elsewhere herein). According to some embodiments, the database may be generated by calculating a plurality of predicted signals for a predicted set of coordinates of the magnetic element. According to some embodiments, the database may be generated by calculating a plurality of predicted signals based, at least in part, on the received signals associated with the sample set of coordinates. According to some embodiments, the coordinates of the predicted set of coordinates may be different from coordinates of the sample set of coordinates. According to some embodiments, the sample set may include a plurality of different spatial locations and/or plurality of orientations of the magnetic element in relation to the array. According to some embodiments, the predicted set of coordinates may include a plurality of spatial locations and/or plurality of orientations of the magnetic element in relation to the array.

For example, according to some embodiments, the predicted set of coordinates may include one or more coordinates (or spatial locations) that the sample set (or obtained data set) does not include. For example, according to some embodiments, the predicted set of coordinates may include one or more orientations of the magnetic element that the sample set does not include.

According to some embodiments, the sample set may include a plurality of coordinates with a same x-axis value and a same y-axis value, wherein the z-axis value of two or more different coordinates in the sample set is different. According to some embodiments, the sample set may include a plurality of coordinates having a same x-axis value, a same y-axis value, a same z-axis value, and a different orientation (or different degree of rotation) in relation to the array. According to some embodiments, the sample set may include about 1 to 6 coordinates.

Advantageously, extrapolating one or more data sets of the database enables determining the spatial location and/or orientation of a medical tool (or the magnetic element positioned on the medical took, in relation to the array of (magnetic) sensors) for spatial locations and/or orientations which were not priorly obtained. Thus, calculating one or more data sets of the database enables generating a database which comprises a plurality of spatial locations and/or orientations of the medical tool which are not predicted in advance (or in other words, did not need to be foreseen by a user during generation of the database).

According to some embodiments, the deep learning algorithm may be further configured to determine the spatial location and/or orientation of a plurality of medical tools within the body. According to some embodiments, the algorithm may be further configured to determine the spatial location and/or orientation of a plurality of medical tools within the body using superposition of the signals saved within the database.

Advantageously, the generated database, which may be generated using one magnetic element (or one medical tool) may be used to determine the spatial location and/or orientation of two or more medical tools.

According to some embodiments, the system may be configured for operating a remote medical tool. According to some embodiments, the system may include a magnetic element, such as magnetic element 106. According to some embodiments, the system may include an array of magnetic sensors, such as the array of magnetic sensors 104. According to some embodiments, the array of magnetic sensors may be configured to detect a change in magnetic field generated by a movement of the magnetic element. According to some embodiments, the system may include a remote medical tool configured to be used during operation within a patient's body. According to some embodiments, the remote medical tool may be positioned such that movements thereof may not be detected using the array of magnetic sensors.

According to some embodiments, the system may include a processor, such as the processor 108. According to some embodiments, the processor may be operative communication with the remote medical tool. According to some embodiments, the processor may control the coordinate, orientation, and/or spatial location of the remote medical tool.

According to some embodiments, the processor may be configured to detect a change in magnetic field and/or determine the spatial location and/or orientation of the magnetic element. According to some embodiments, detect a change in magnetic field and/or determine the spatial location and/or orientation of the magnetic element based on one or more deep learning algorithm(s) correlating the change of the magnetic field with the spatial location and/or orientation of the magnetic element. According to some embodiments, the processor may be configured to translate the movement of the magnetic element into a command for the remote medical tool, based, at least in part, on the determined spatial location and/or orientation of the magnetic element.

Figure 2:
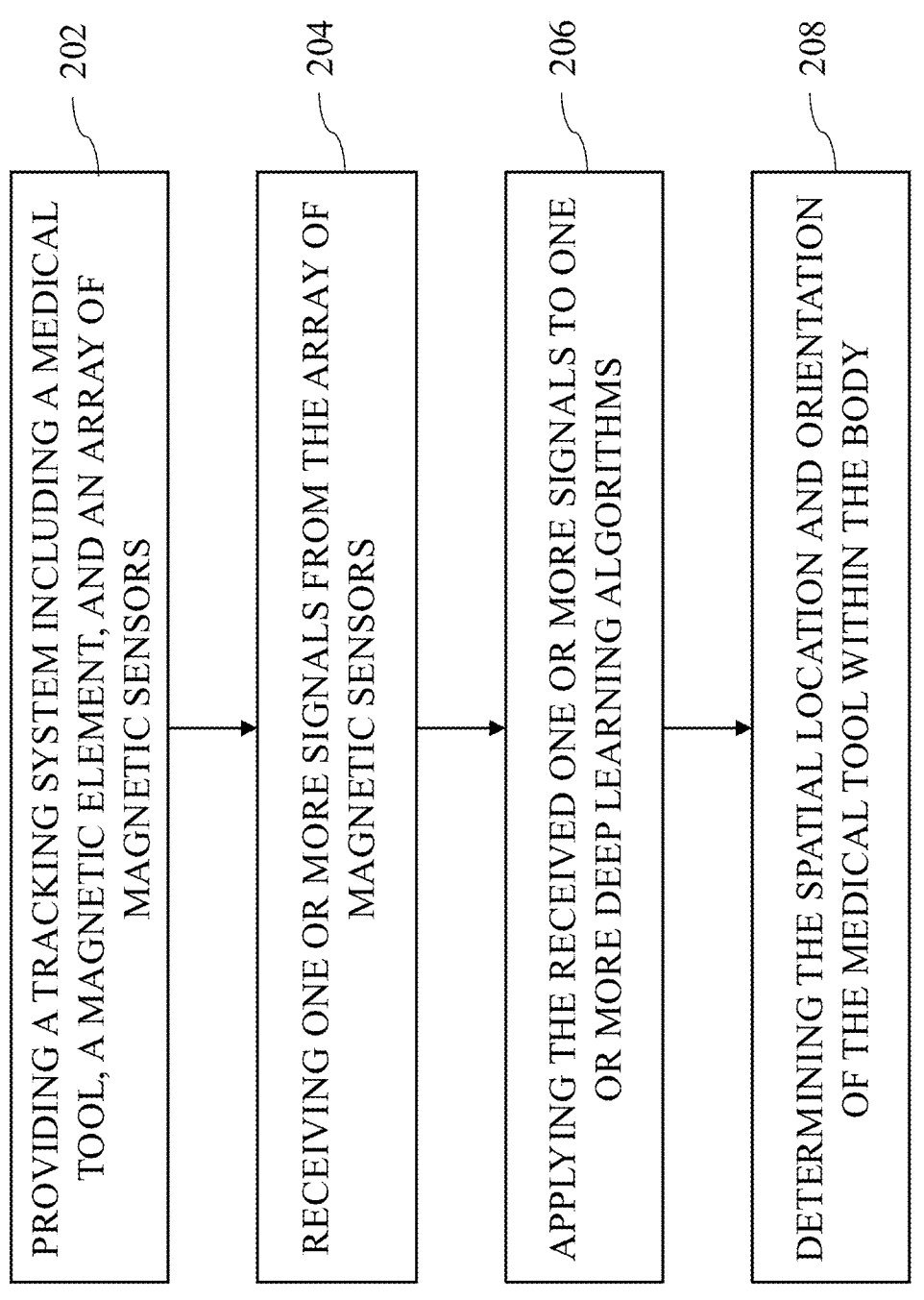
FIG. 2 shows a flowchart of functional steps in a method for tracking a medical tool inside a subject's body during a medical procedure, in accordance with some embodiments of the present invention.

Reference is made to FIG. 2, which shows a flowchart of functional steps in a method for tracking a medical tool inside a subject's body during a medical procedure, in accordance with some embodiments of the present invention.

According to some embodiments, the method may include, at step 202, providing a tracking system, such as, for example, tracking system 100, including a medical tool, such as, for example, medical tool 102, and a magnetic element, such as, for example, magnetic element 106, and an array of magnetic sensors, such as, for example, the array of magnetic sensors 104. According to some embodiments, the method may include positioning the array of magnetic sensors 104 beside and/or on the subject during an operation. According to some embodiments, the method may include inserting the medical tool 102 into the body of the subject, for example, towards the surgical site.

According to some embodiments, the method may include, at step 204, receiving one or more signals from the array of magnetic sensors 104. According to some embodiments, the method may include receiving one or more signals from one or more individual sensor of the plurality of sensors 116. According to some embodiments, the method may include receiving one or more signals from each individual sensor of the plurality of sensors 116. According to some embodiments, the method may include receiving three signals from one or more individual sensor of the plurality of sensors 116. According to some embodiments, the method may include receiving three signals from each individual sensor of the plurality of sensors 116. According to some embodiments, at least one signal is associated with a change in the magnetic field in the x-axis in relation to the array of magnetic sensors 104. According to some embodiments, at least one signal is associated with a change in the magnetic field in the y-axis in relation to the array of magnetic sensors 104. According to some embodiments, at least one signal is associated with a change in the magnetic field in the z-axis in relation to the array of magnetic sensors 104.

According to some embodiments, at step 206, the method may include applying the received one or more signals to one or more deep learning algorithms. According to some embodiments, the one or more deep learning algorithms may include one or more of a convolutional neural network algorithm, multilayer perceptron algorithm, XGBoost algorithm, recurrent neural network algorithm, and the like. According to some embodiments, the one or more deep learning algorithms may be in communication with the database. According to some embodiments, the one or more deep learning algorithms may be configured to determine the spatial location and/or orientation of the magnetic element 106 in relation to the array of magnetic sensors 104. According to some embodiments, the one or more deep learning algorithms and/or the processor 108 may be configured to determine the spatial location and/or orientation of the medical tool 102 in relation to the array of magnetic sensors 104 using the determined spatial location and/or orientation of the magnetic element 106.

According to some embodiments, the method may include, at step 208, determining the spatial location and/or orientation of the medical tool 102 within the body of the subject. According to some embodiments, the method may include determining the spatial location and/or orientation of the medical tool 102 based, at least in part, on the one or more deep learning algorithms correlating the change of the magnetic field with the spatial location and/or orientation of the magnetic element 106. According to some embodiments, the method may include determining the spatial location and/or orientation of the medical tool 102 based, at least in part, on data stored within the database.

Advantageously, determining the spatial location and/or orientation of the medical tool 102 by applying deep learning algorithms to the one or more signals received from the array of magnetic sensors 104 enables the tracking the medical tool 102 without applying mathematical calculations. According to some embodiments, the method for tracking a medical tool inside a subject's body during a medical procedure does not necessitate applying the one or more signals received from the array of magnetic sensors 104 to a mathematical formula, or in other words, the method does not estimate the spatial location and/or orientation of the medical tool 102. Mathematical formulas that are used to obtain the spatial location and/or orientation of a medical tool quantitatively estimate of the spatial location and/or orientation and are limited to the resolution of the mathematical formula itself, which commonly includes rounding one or more values.

Advantageously, the method may include tracking a medical tool inside a subject's body during a medical procedure without applying the data received from the array of magnetic sensors 104 to a mathematical formula. For example, according to some embodiments, the data received from the plurality of sensors are applied to the one or more deep learning algorithms such that the deep learning algorithm outputs the spatial location and/or orientation of the medical tool 102 based, at least in part, on the received magnetic data. Thus, the resolution of the determined spatial location and/or orientation using the one or more deep learning algorithms is greater than a resolution of tracking methods that use mathematical formulas, which are limited to the precision and/or resolution of the mathematical formula.

According to some embodiments, the precision between the determined spatial location and/or orientation of the deep learning algorithm and the actual location and/or orientation, or in other words, the accuracy of the determined spatial location and/or orientation, may be smaller than 0.5 mm. According to some embodiments, the actual location and/or orientation may be the location and/or orientation of the magnetic element 106 and/or the medical tool 102 in relation to the array of magnetic sensors 104.

Advantageously, determining the spatial location and/or orientation of the medical tool 102 by applying deep learning algorithms to the one or more signals received from the array of magnetic sensors 104 enables the tracking the medical tool 102 without generating a model, such as a 2D model or a 3D model, of the surgical site and the medical tool 102 in relation to the surgical site. According to some embodiments, the method for tracking a medical tool inside a subject's body during a medical procedure does not necessitate generating a model of the medical tool 102 and/or magnetic element 106 in relation to the array of magnetic sensors 104 in order to determine the spatial location and/or orientation of the medical tool 102.

According to some embodiments, determining the spatial location and/or orientation of the medical tool 102 comprises compensating for a dimension of the medical tool 102 in relation to the location of the magnetic element 106 in relation to the medical tool 102. According to some embodiments, the method may include receiving input associated with a type of medical tool used in the procedure. According to some embodiments, the method may include comprises compensating for a dimension of the medical tool 102 in relation to the location of the magnetic element 106 based, at least in part, on the inputted type of medical tool. According to some embodiments, method may include receiving input associated with a location, position, and/or orientation of the magnetic element 106 in relation to the medical tool 102. According to some embodiments, the method may include comprises compensating for a dimension of the medical tool 102 in relation to the location of the magnetic element 106 based, at least in part, on the inputted location, position, and/or orientation of the magnetic element 106 in relation to the medical tool 102.

According to some embodiments, the method may include outputting the coordinates of the spatial location of the medical tool. According to some embodiments, the method may include outputting the orientation of the medical tool. According to some embodiments, the output may be displayed onto a display. According to some embodiments, the method may include displaying the spatial location and/or orientation of the medical tool in relation to the surgical site, such as, for example, on a scan of the subject. According to some embodiments, the method may include registering the determined spatial location and/or orientation of the medical tool within the body to a scan of the subject. According to some embodiments, the method may include registering the determined spatial location and/or orientation of the medical tool within the body to a scan of the subject in real time.

According to some embodiments, the method may include compensating for variations in the change of the magnetic field associated with one or more of a type of tissue, a type of procedure, a type of medical tool, and characteristics of the subject. According to some embodiments, the characteristics of the subject comprise one or more of the age, gender, weight, and medical history of the subject.

Reference is made to FIG. 3, which shows a flowchart of functional steps in a method for generating a database, in accordance with some embodiments of the present invention. According to some embodiments, the method 200 may include one or more steps of method 300. According to some embodiments, the method 300 may include one or more steps of method 200.

According to some embodiments, at step 302, the method 300 may include providing the tracking system which may include the magnetic element (such as, for example, the magnetic element 104) and the array of magnetic sensors (such as, for example, the array of magnetic sensors 106). According to some embodiments, at step 304, the method 300 may include positioning the magnetic element at a sample set of coordinates. According to some embodiments, at step 306, the method 300 may include receiving one or more signals associated with each coordinate of the sample set of coordinates of the magnetic element. According to some embodiments, at step 308, the method 300 may include calculating a plurality of predicted signals for a predicted set of coordinates of the magnetic element, based, at least in part, on the received signals associated with the sample set of coordinates.

According to some embodiments, and as described in greater detail elsewhere herein, the coordinates of the predicted set of coordinates are different from coordinates of the sample set of coordinates. According to some embodiments, the term "sample set" and "sample set of coordinates" may be used interchangeably. According to some embodiments, the sample set of coordinates may include a plurality of different spatial locations and/or plurality of orientations of the magnetic element in relation to the array. According to some embodiments, the predicted set of coordinates may include a plurality of spatial locations and/or plurality of orientations of the magnetic element in relation to the array. According to some embodiments, the sample set of coordinates may include a plurality of coordinates with a same x-axis value and a same y-axis value, wherein the z-axis value of two or more different coordinates in the sample set of coordinates is different. According to some embodiments, the sample set of coordinates may include a plurality of coordinates having a same x-axis value, a same y-axis value, a same z-axis value, and a different orientation (or different degree of rotation) in relation to the array. According to some embodiments, the sample set of coordinates comprises about 1 to 6 coordinates.

Advantageously, generating the database enables determining the spatial location and/or orientation of a medical tool (or the magnetic element positioned on the medical took, in relation to the array of magnetic sensors) for spatial locations and/or orientations which were not priorly obtained. According to some embodiments, generating the database may include determining (or calculating) a plurality of spatial locations and/or orientations of the medical tool which are not predicted in advance (or in other words, did not need to be foreseen by a user during generation of the database).

According to some embodiments, the deep learning algorithm may be configured to determine the spatial location and/or orientation of a plurality of medical tools within the body. According to some embodiments, the algorithm may be further configured to determine the spatial location and/or orientation of a plurality of medical tools within the body using superposition calculations of the signals saved within the database.

Advantageously, the generated database, which may be generated using one magnetic element (or one medical tool) may be used to determine the spatial location and/or orientation of two or more medical tools.

Reference is made to FIG. 4, which shows a flowchart of functional steps in a method for operating a remote medical tool, in accordance with some embodiments of the present invention. According to some embodiments, the method 400 may include one or more steps of any one of methods 200/300. According to some embodiments, any one of the methods 200/300 may include one or more steps of method 400.

According to some embodiments, the method 400 may be configured for operating (or controlling) a remote medical tool using a tracking system as disclosed herein. According According to some embodiments, at step 402, the method 400 may include providing a magnetic element and an array of magnetic sensors, wherein the array is configured to detect a change in magnetic field generated by a movement of the magnetic element. According to some embodiments, at step 404, the method 400 may include detecting, utilizing a processor, the change in magnetic field and determining the spatial location and/or orientation of the magnetic element, based on one or more deep learning algorithm(s) correlating the change of the magnetic field with the spatial location and/or orientation of the magnetic element. According to some embodiments, at step 406, the method 400 may include translating the movement of the magnetic element into a command for a remote medical tool, based, at least in part, on the determined spatial location and/or orientation of the magnetic element. According to some embodiments, the remote medical tool comprises a motor configured to receive the command from the processor and operate the remote medical tool.

According to some embodiments, translating the movement of the magnetic element into a command may include adjusting the proportion between the movement of the magnetic element and the command such that movement of the remote medical tool may be proportionately smaller or larger than the movement of the magnetic element. For example, the movement of the magnetic element may be 5 times larger than the command (or the movement of the remote medical tool), such that an advance of 5 centimeters (cm) of the magnetic element results in an advance of 1 cm in the same direction and/or orientation.

According to some embodiments, the system as described herein may be used to simulate a medical operation. According to some embodiments, the method may include generating a simulation of a medical operation. According to some embodiments, the remote medical tool may be a simulated medical tool in the simulation of a medical operation, and wherein translating the movement of the magnetic element into a command comprises displaying the movement of the simulated medical tool in the simulated medical operation.

In the description and claims of the application, the words "include" and "have", and forms thereof, are not limited to members in a list with which the words may be associated.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although stages of methods according to some embodiments may be described in a specific sequence, methods of the disclosure may include some or all of the described stages carried out in a different order. A method of the disclosure may include a few of the stages described or all of the stages described. No particular stage in a disclosed method is to be considered an essential stage of that method, unless explicitly specified as such.

Although the disclosure is described in conjunction with specific embodiments thereof, it is evident that numerous alternatives, modifications and variations that are apparent to those skilled in the art may exist. Accordingly, the disclosure embraces all such alternatives, modifications and variations that fall within the scope of the appended claims. It is to be understood that the disclosure is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the disclosure. Section headings are used herein to ease understanding of the specification and should not be construed as necessarily limiting.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

The deep learning algorithm included a convolutional neural network. The deep learning algorithm included three convolutional layers. The last convolutional layer included a max pooling layer, such as maxpooling2d. After the last convolutional layer, the algorithm included a lineal layer having 256 neurons and an additional hidden layer of 40 neurons, followed by an output layer. An activation layer, such as the rectified linear activation function (ReLU), was placed between each of the abovementioned layers.

Example 2

The deep learning algorithm included a multilayer perceptron algorithm. The algorithm included one input layer, four hidden layers, and followed by an output layer. An activation layer, such as the gaussian error linear unit (GELU), was placed between each of the abovementioned layers. Using the multilayer perceptron algorithm, the average deviation between the determined spatial location and/or orientation and the actual spatial location and/or orientation was 0.6 mm.

Example 3

The deep learning algorithm included a XGBoost algorithm. A mean square error (MSE) loss function was used applied the XGBoost algorithm. Using the XGBoost algorithm, the average deviation between the determined spatial location and/or orientation and the actual spatial location and/or orientation was about 1 mm.

Example 4

The deep learning algorithm included a recurrent neural network. The algorithm included models such as embedding, masking, long short-term memory (LSTM), dropout, and dense. An activation layer, such as the rectified linear activation function (ReLU), as well as a mean square error (MSE) loss function were applied between each of the abovementioned layers. Using the recurrent neural network, the average deviation between the determined spatial location and/or orientation and the actual spatial location and/or orientation was 1 mm.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for tracking a medical tool during a medical procedure, the method comprising:

providing a tracking system comprising a medical tool comprising a magnetic element; and an array of magnetic sensors;

wherein the array of magnetic sensors is configured to detect a change in a magnetic field generated by movement of the magnetic element within the body; and determining, utilizing a processor, the spatial location and/or orientation of the medical tool within a body of a subject, based on one or more deep learning algorithms trained on a database comprising signal sets corresponding to known and predicted coordinates, the deep learning algorithms correlating the change of the magnetic field with spatial location and/or orientation of the magnetic element.

2. The method according to claim 1, wherein determining the spatial location and/or orientation of the medical tool comprises compensating for a dimension of the medical tool in relation to the location of the magnetic element in relation to the medical tool.

3. The method according to claim 1, wherein the array of magnetic sensors is configured in a cartesian, radial, or cylindrical coordinate system.

4. The method according to claim 1, wherein the array of magnetic sensors is configured to wirelessly associate with the magnetic element and/or the medical tool.

5. The method according to claim 1, wherein determining the spatial location and/or orientation of the medical tool comprises compensating for variations in the magnetic field associated with one or more of a type of tissue, a type of procedure, a type of medical tool, and characteristics of the subject.

6. The method according to claim 1, further comprising registering the determined spatial location and/or orientation of the medical tool within the body to a scan of the subject.

7. The method according to claim 1, wherein the processor is configured to train the deep learning algorithm on a training set comprising a database associated with the changes of the magnetic field due to a change of one or more coordinates of the magnetic element.

8. The method according to claim 7, wherein the database comprises data obtained by receiving one or more signals associated with a change of the magnetic field generated by a change in the spatial location and/or orientation of the magnetic element between a plurality of pairs of coordinates; and/or wherein the database comprises data sets obtained using the array of magnetic sensors, and wherein each of the data sets comprises three signals from each individual sensor of the array of magnetic sensors for each change in spatial location or orientation of the magnetic element.

9. The method according to claim 7, wherein a change in the spatial location and/or orientation of the magnetic element comprises a translation of the magnetic element in one or more axes at a specified distance.

10. The method according to claim 7, wherein a change in the spatial location and/or orientation of the magnetic element comprises a rotation of the magnetic element at a specified degree of rotation.

11. The method according claim 10, wherein the rotation of the magnetic element comprises rotation about at least one of a longitudinal axis of the magnetic element, a lateral axis of the magnetic element, and a vertical axis of the magnetic element.

12. The method according to claim 7, wherein the database is generated by:
   providing the tracking system comprising the magnetic element and the array of magnetic sensors;
   positioning the magnetic element at a sample set of coordinates;
   receiving one or more signals associated with each coordinate of the sample set of coordinates of the magnetic element; and
   calculating a plurality of predicted signals for a predicted set of coordinates of the magnetic element, based, at least in part, on the received signals associated with the sample set of coordinates, wherein the coordinates of the predicted set of coordinates are different from coordinates of the sample set of coordinates.

13. The method according to claim 12, wherein the sample set of coordinates comprises a plurality of different spatial locations and/or plurality of orientations of the magnetic element in relation to the array of magnetic sensors; and/or
   wherein the predicted set of coordinates comprises a plurality of spatial locations and/or
   plurality of orientations of the magnetic element in relation to the array.

14. The method according to claim 12, wherein the sample set of coordinates comprises a plurality of coordinates with a same x-axis value and a same y-axis value, wherein the z-axis value of two or more different coordinates in the sample set of coordinates is different; and/or
   wherein the sample set of coordinates comprises a plurality of coordinates having a same x-axis value, a same y-axis value, a same z-axis value, and a different orientation or different degree of rotation in relation to the array of magnetic sensors.

15. The method according to claim 12, wherein the deep learning algorithm is further configured to determine the spatial location and/or orientation of a plurality of medical tools within the body.

16. A system for tracking a medical tool during a medical procedure, the system comprising:
   a tracking system comprising:

a magnetic element configured to be placed onto a remote controlled medical tool, and
   an array of magnetic sensors, wherein the array of magnetic sensors is configured to detect a change in a magnetic field generated by movement of the magnetic element; and
   a processor configured to receive the detected change in the magnetic field and determine the spatial location and/or orientation of the medical tool, based on one or more deep learning algorithms trained on a database comprising signal sets corresponding to known and predicted coordinates, said deep learning algorithm(s) correlating the change of the magnetic field with spatial location and/or orientation of the magnetic element.

17. A method for operating a remote medical tool, the method comprising:
   providing a magnetic element and an array of magnetic sensors, wherein the array of magnetic sensors is configured to detect a change in a magnetic field generated by a movement of the magnetic element;
   detecting, utilizing a processor, the change in the magnetic field and determining the spatial location and/or orientation of the magnetic element, based on one or more deep learning algorithm trained on a database comprising signal sets corresponding to known and predicted coordinates, said deep learning algorithms correlating the change of the magnetic field with spatial location and/or orientation of the magnetic element; and
   translating the movement of the magnetic element into a command for a remote medical tool, based, at least in part, on the determined spatial location and/or orientation of the magnetic element.

18. The method according to claim 17, wherein the remote medical tool comprises a motor configured to receive the command from the processor and operate the remote medical tool.

19. The method according to claim 17, further comprising generating a simulation of a medical operation, wherein the remote medical tool is a simulated medical tool in the simulation of a medical operation, and wherein translating the movement of the magnetic element into a command comprises displaying the movement of the simulated medical tool in the simulated medical operation.

20. The method according to claim 17, wherein translating the movement of the magnetic element into a command further comprises adjusting the proportion between the movement of the magnetic element and the command such that movement of the remote medical tool may be proportionately smaller or larger than the movement of the magnetic element.

* * * * *